US010698498B2

(12) United States Patent
Silva Arce et al.

(10) Patent No.: US 10,698,498 B2
(45) Date of Patent: Jun. 30, 2020

(54) CONFIGURABLE DEVICE SWITCHING MECHANISM THAT ENABLES SEAMLESS INTERACTIONS WITH MULTIPLE DEVICES

(71) Applicant: Komodo OpenLab Inc., Toronto (CA)

(72) Inventors: Jorge Silva Arce, Toronto (CA); Mauricio Meza, Toronto (CA); Tom Nantais, Toronto (CA); Lawrence Kwok, Toronto (CA)

(73) Assignee: Komodo OpenLab Inc., Toronto, Ontario (CA)

( * ) Notice: Subject to any disclaimer, the term of this patent is extended or adjusted under 35 U.S.C. 154(b) by 0 days.

(21) Appl. No.: 16/204,090

(22) Filed: Nov. 29, 2018

(65) Prior Publication Data

US 2019/0163283 A1      May 30, 2019

Related U.S. Application Data

(60) Provisional application No. 62/592,938, filed on Nov. 30, 2017.

(51) Int. Cl.
*G06F 3/01*       (2006.01)
*G06K 9/00*       (2006.01)
(Continued)

(52) U.S. Cl.
CPC ............. *G06F 3/017* (2013.01); *G06F 3/038* (2013.01); *G06F 21/305* (2013.01);
(Continued)

(58) Field of Classification Search
CPC ........ G06F 3/017; G06F 3/038; G06F 3/0484; G06F 3/04842; G06F 3/04845;
(Continued)

(56) References Cited

U.S. PATENT DOCUMENTS 5,481,265 A      1/1996  Russell
5,523,745 A *    6/1996  Fortune ..................... A61F 4/00
                                                   340/4.12
(Continued)

OTHER PUBLICATIONS

Schauer et al., "Simple Electrical Transducer (SET) Standard", Computer Access Program, University Affiliated Programs, The Trace Center, University of Wisconsin-Madison, 2016 (2 pages) <https://park.org/Guests/Trace/pavilion/setdoc.htm>.
(Continued)

*Primary Examiner* — Tom V Sheng
(74) *Attorney, Agent, or Firm* — Bereskin & Parr LLP/S.E.N.C.R.L., s.r.l.; Tony Orsi

(57) ABSTRACT

Various embodiments are described herein for an assistive device and associated method for interacting with at least one electronic device. In one example embodiment, the assistive device can include at least one communication interface, a memory, and at least one processing unit. The memory can store a whitelist of the at least one electronic device; and a gesture-to-command map of input signals in linked association with commands, including a selection command and a control command. The processing unit can be configured for sustaining an electronic communication connection to a target electronic device; receiving an input signal generated from user manipulation of a physical interface; searching the gesture-to-command map based on the input signal to determine a command; and using the at least one communication interface to transmit the command to the at least one electronic device thereby allowing the user to use the same assistive device for selecting and/or controlling at least one electronic device.

26 Claims, 5 Drawing Sheets

(51) Int. Cl.
*G06F 21/30* (2013.01)
*H04L 29/06* (2006.01)
*H01H 13/00* (2006.01)
*G06F 3/038* (2013.01)
*A61B 5/00* (2006.01)

(52) U.S. Cl.
CPC ......... *G06K 9/00389* (2013.01); *H01H 13/00* (2013.01); *H04L 63/101* (2013.01); *A61B 5/74* (2013.01)

(58) Field of Classification Search
CPC .. G06F 3/04847; G06F 3/0486; G06F 3/0487; G06F 3/0488; G06F 3/0489; G06F 19/00; G06F 21/305; G06K 9/00389; H01H 13/00; H04L 63/101; A61B 5/74
See application file for complete search history.

(56) References Cited

U.S. PATENT DOCUMENTS

| | | | |
|---|---|---|---|
| 6,833,786 B1 | 12/2004 | Sun et al. | |
| 7,535,401 B2 | 5/2009 | Tolmei | |
| 8,433,828 B2 | 4/2013 | Fleizach et al. | |
| 8,963,694 B2 | 2/2015 | Nystrom et al. | |
| 9,081,810 B1* | 7/2015 | Smith | G06F 16/24 |
| 2011/0302532 A1* | 12/2011 | Missig | G06F 3/0416 715/823 |
| 2012/0151420 A1* | 6/2012 | Amento | G06F 3/017 715/863 |
| 2013/0069985 A1* | 3/2013 | Wong | G02B 27/017 345/633 |
| 2014/0196142 A1* | 7/2014 | Louboutin | G06F 21/44 726/16 |
| 2015/0011247 A1* | 1/2015 | Ezra | G06F 3/017 455/456.3 |
| 2016/0021168 A1* | 1/2016 | Chaudhri | H04L 67/025 715/740 |
| 2016/0054791 A1* | 2/2016 | Mullins | G04G 21/00 345/173 |
| 2016/0300028 A1* | 10/2016 | Abell | G06F 9/44505 |
| 2016/0337689 A1* | 11/2016 | Yoshimura | H04N 21/42607 |
| 2017/0123487 A1* | 5/2017 | Hazra | G06F 3/015 |
| 2017/0185383 A1* | 6/2017 | Sarkar | G06F 3/04842 |
| 2018/0359307 A1* | 12/2018 | Mujibiya | G06F 16/27 |

OTHER PUBLICATIONS

Torrini, "USB HID usage table", 2006, webpage accessed on Nov. 27, 2017 (20 pages) <http://www.freebsddiary.org/APC/usb_hid_usages.php>.

Farrall et al., "Switch Accessible Apps for iPad/iPhone", review, 2012 (21 pages) <http://www.janefarrall.com/html/resources/Switch%20Accessible%20Apps%20for%20iPad.pdf>.

Amazon.com, Inc., "Alexa Skills", webpage accessed on Nov. 27, 2017 (2 pages) <https://www.amazon.com/b?node=13727921011>.

IFTTT, 2016, webpage accessed on Nov. 27, 2017 (39 pages) <https://ifttt.com/search/services>.

* cited by examiner

CONFIGURABLE DEVICE SWITCHING MECHANISM THAT ENABLES SEAMLESS INTERACTIONS WITH MULTIPLE DEVICES

CROSS-REFERENCE TO RELATED APPLICATION

This application claims the benefit of U.S. Provisional Patent Application No. 62/592,938, filed on Nov. 30, 2017, which is incorporated herein by reference in its entirety.

FIELD

The present disclosure relates to the field of assistive devices for individuals with physical impairments, and in particular, to assistive devices that enable individuals with physical impairments to interact more easily with multiple devices.

BACKGROUND

The daily routine of an individual can involve interacting with multiple home appliances and/or electronic devices. Able-bodied individuals can choose the appliance and/or device that they want to engage with, at any given time, by directly manipulating the appliance and/or device through a variety of standard physical interfaces. Standard physical interfaces can include, but are not limited to, buttons, switches, keyboards, keypads, dials, levers, remote controls, and pointing devices such as touch screens.

However, some individuals can have physical impairments that prevent them from using these standard physical interfaces and they may instead have to rely on simplified switch input devices adapted to their unique physical abilities. A button is an example of a simplified switch input device. A switch interface can be provided to relay switching events from the simplified switch input device to a particular appliance. However, since different appliances often respond to different switching events, switch interfaces must typically be reconfigured for a particular appliance in order to control it. Generally, reconfiguration cannot be performed using the simplified switch input. Therefore, individuals with physical impairments may require the assistance of a third party in order to reconfigure a switch interface for use with an appliance that it is not currently configured to interact with.

Some conventional switch interfaces for able-bodied individuals enable the control of multiple electronic devices. For example, a wireless keyboard can be used to send text and/or commands to a variety of target electronic devices (e.g., mobile devices). However, the selection of a target electronic device is typically performed using an additional selection mechanism, such as a slider switch or selector wheel that is included in the wireless keyboard for the sole purpose of selecting a target appliance. Users who do not have the dexterity to manipulate the slider switch or selector wheel are not able to independently choose which electronic device they want to control with the keyboard.

SUMMARY OF VARIOUS EMBODIMENTS

In a broad aspect, at least one embodiment described herein provides an assistive device for interacting with at least one electronic device. The assistive device may comprise at least one communication interface, a memory, and at least one processing unit. The memory may store a whitelist of the at least one electronic device; and a gesture-to-command map. The gesture-to-command map may comprise a plurality of input signals, each input signal in linked association with one of a plurality of commands. The plurality of commands may comprise at least one selection command and at least one control command. The processing unit can be configured for: using the at least one communication interface to sustain an electronic communication connection to a target electronic device that is in the whitelist; receiving at least one input signal generated from user manipulation of at least one physical interface; searching the gesture-to-command map based on the at least one input signal to determine a target command; and using the at least one communication interface to transmit the target command to the at least one electronic device.

In at least one embodiment, the assistive device may further comprise the at least one physical interface.

In at least one embodiment, the at least one physical interface may comprise a releasably depressable cover of the assistive device; and a switch coupled to the releasably depressable cover for generating an input signal when the cover is depressed.

In at least one embodiment, the switch may comprise a first switch activation surface, a base, and at least one releasably depressable member. The first switch activation surface may be mounted to an inner surface of the releasably depressable cover of the assistive device. The base may be coupled to the releasably depressable cover and have a second switch activation surface facing the first switch activation surface. The at least one releasably depressable member may be positioned between the first switch activation surface and the second switch activation surface. The at least one releasably depressable member may have a first height when not depressed and a second height when depressed. The first height may be higher than a plane defined by the second switch activation surface to provide a gap between the first switch activation surface and the second switch activation surface, and the second height may be lower than the plane defined by the second switch activation surface to permit contact between the first switch activation surface and the second switch activation surface.

In at least one embodiment, the at least one physical interface may comprise a touch-sensitive surface of the assistive device, and a track pad coupled to the touch-sensitive surface for generating an input signal when an external force is applied to the touch-sensitive surface.

In at least one embodiment, the assistive device may further comprise at least one peripheral port for connecting a physical interface of the at least one physical interface to the assistive device.

In at least one embodiment, the at least one electronic device may comprise at least one locally connectable electronic device; and the processing unit may be further configured for using the at least one communication interface to pair to the locally connectable electronic device; and adding the locally connectable electronic device to the whitelist.

In at least one embodiment, the at least one electronic device may comprise at least one remotely connectable electronic device; and the processing unit may be further configured for providing authentication information to a device management server that is in electronic communication with the remotely connectable electronic device; and adding the remotely connectable electronic device to the whitelist.

In at least one embodiment, when the target electronic device is a remotely connectable electronic device, the at least one communication interface may be used to transmit the target command to the target electronic device by transmitting the target command to the device management server.

In at least one embodiment, the at least one communication interface may be used to transmit an innocuous command to the target electronic device in order to sustain the electronic communication connection to the target electronic device.

In at least one embodiment, the processing unit may be further configured to attempt to re-establish the electronic communication to the target electronic device in response to determining that an electronic communication connection to a target electronic device has failed.

In at least one embodiment, the processing unit may be further configured to establish an electronic communication connection to another target electronic device in the whitelist in response to determining that an electronic communication connection to a target electronic device has failed.

In at least one embodiment, the at least one electronic device may comprise at least two electronic devices and the target command may comprise a selection command. The sustaining an electronic communication connection to a target electronic device may comprise sustaining an electronic communication connection to a first target electronic device. The searching the gesture-to-command map based on the at least one input signal to determine a target command may comprise searching the gesture-to-command map to determine that the at least one input signal corresponds to the selection command. The using the at least one communication interface to transmit the target command to the at least one electronic device may comprise establishing and sustaining an electronic communication connection to a second target electronic device in the whitelist.

In at least one embodiment, the sustenance of the electronic communication connection to the first target electronic device may be discontinued when an electronic communication connection to a second target electronic device has been established and sustained.

In at least one embodiment, the at least one electronic device may comprise at least two electronic devices and the target command may comprise a device-specific control command. The sustaining an electronic communication connection to a target electronic device may comprise sustaining an electronic communication connection to a first target electronic device. The searching the gesture-to-command map based on the at least one input signal to determine a target command may comprise searching the gesture-to-command map to determine that the at least one input signal corresponds to the device-specific control command, the device-specific control command corresponding to a second target electronic device in the whitelist. The using the at least one communication interface to transmit the target command to the at least one electronic device may comprise using the at least one communication interface to transmit the device-specific command to the second target electronic device.

In at least one embodiment, the target command may comprise a generic control command. The sustaining an electronic communication connection to a target electronic device may comprise sustaining an electronic communication connection to a first target electronic device. The searching the gesture-to-command map based on the at least one input signal to determine a target command may comprise searching the gesture-to-command map to determine that the at least one input signal corresponds to the generic control command. The using the at least one communication interface to transmit the target command to the at least one electronic device may comprise using the at least one communication interface to transmit the generic control command to the first target electronic device.

In at least one embodiment, the gesture-to-command map may be configurable by a user.

In at least one embodiment, the assistive device may further comprise an electrical energy storage component for providing power to components of the assistive device.

In at least one embodiment, the processing unit may be further configured for using the at least one communication interface to receive data from the at least one electronic device.

In at least one embodiment, the whitelist may comprise information for managing electronic communication connections to the at least one electronic device.

In another broad aspect, at least one embodiment described herein provides a method for interacting with at least one electronic device. The method may comprise providing an assistive device having a memory and at least one communication interface; storing, in the memory, a whitelist of the at least one electronic device and a gesture-to-command map; using the at least one communication interface to sustain an electronic communication connection to a target electronic device that is in the whitelist; receiving, at the assistive device, at least one input signal generated from user manipulation of at least one physical interface; searching the gesture-to-command map based on the at least one input signal to determine a target command; and using the at least one communication interface to transmit the target command to the at least one electronic device. The gesture-to-command map may comprise a plurality of input signals, each input signal in linked association with one of a plurality of commands. The plurality of commands may comprise at least one selection command and a control command.

In another broad aspect, at least one embodiment described herein provides an assistive device for interacting with at least one electronic device, the assistive device comprising: a memory to store: a whitelist including a list of the at least one electronic device; and a gesture-to-command map comprising a plurality of input signals, each input signal in linked association with one of a plurality of commands, the plurality of commands comprising at least one selection command and at least one control command; at least one physical interface for receiving at least one input signal from user manipulation of the at least one physical interface; a gesture analyzer for searching the gesture-to-command map based on the at least one input signal to determine a target command based on the linked command for the at least one input signal; and at least one communication interface to sustain an electronic communication with a target electronic device that is on the whitelist and to transmit the target command to the target electronic device.

BRIEF DESCRIPTION OF THE DRAWINGS

For a better understanding of the various embodiments described herein, and to show more clearly how these various embodiments may be carried into effect, reference will be made, by way of example, to the accompanying drawings which show at least one example embodiment, and which are now described.

Figure 1:
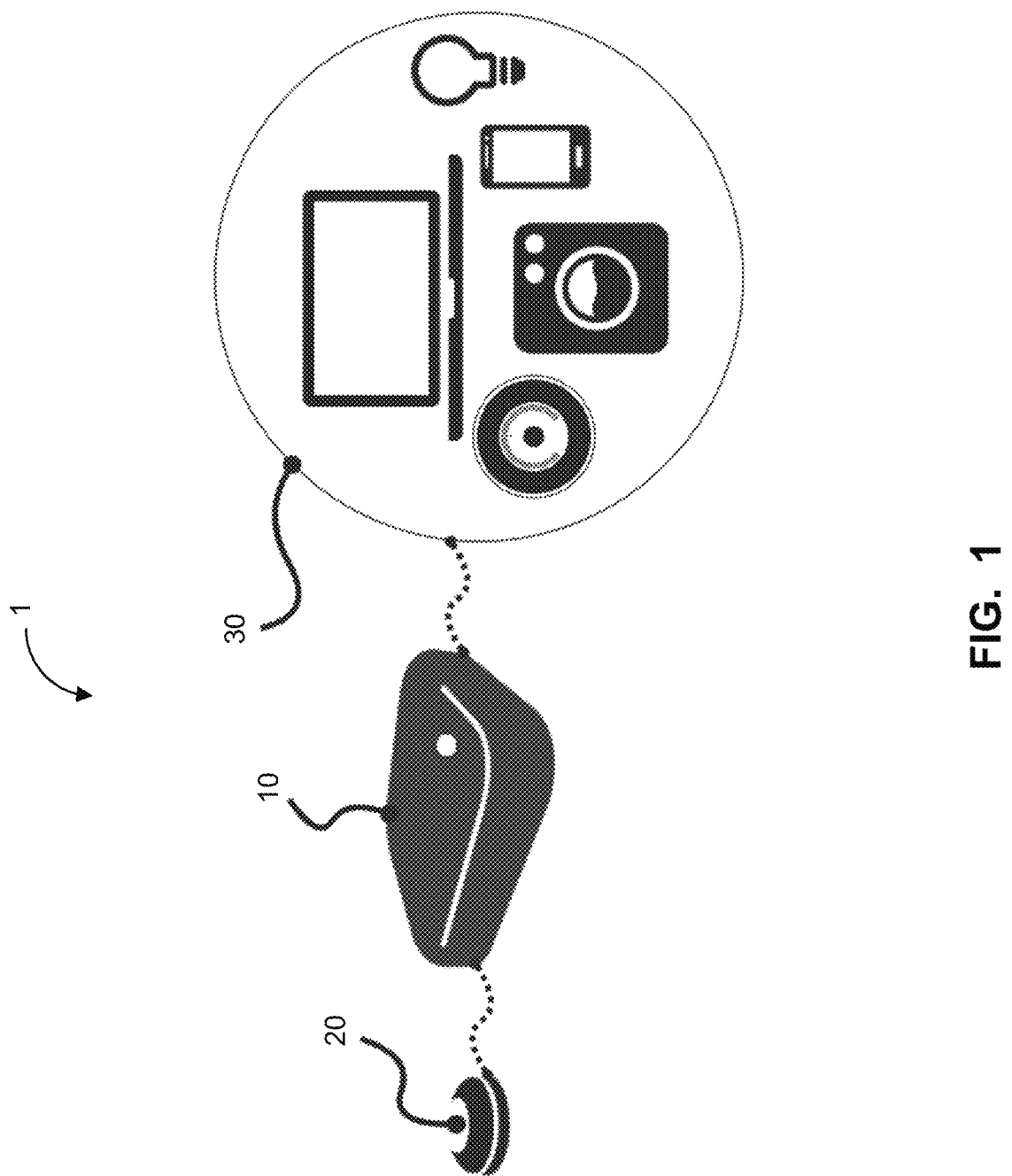
FIG. 1 shows a diagram of an example embodiment of an assistive device that can interact with at least one electronic device.

The skilled person in the art will understand that the drawings, described below, are for illustration purposes only. The drawings are not intended to limit the scope of the applicants' teachings in anyway. Also, it will be appreciated that for simplicity and clarity of illustration, elements shown in the figures have not necessarily been drawn to scale. For example, the dimensions of some of the elements may be exaggerated relative to other elements for clarity. Further, where considered appropriate, reference numerals may be repeated among the figures to indicate corresponding or analogous elements.

DESCRIPTION OF VARIOUS EMBODIMENTS

It will be appreciated that numerous specific details are set forth in order to provide a thorough understanding of the example embodiments described herein. However, it will be understood by those of ordinary skill in the art that the embodiments described herein may be practiced without these specific details. In other instances, well-known methods, procedures and components have not been described in detail so as not to obscure the embodiments described herein. Furthermore, this description is not to be considered as limiting the scope of the embodiments described herein in any way, but rather as merely describing the implementation of the various example embodiments described herein.

The terms "an embodiment", "embodiment", "embodiments", "the embodiment", "the embodiments", "one or more embodiments", "some embodiments", and "one embodiment" mean "one or more (but not all) embodiments of the subject matter described in accordance with the teachings herein", unless expressly specified otherwise.

The terms "including", "comprising" and variations thereof mean "including but not limited to", unless expressly specified otherwise. A listing of items does not imply that any or all of the items are mutually exclusive, unless expressly specified otherwise. In addition, the terms "a", "an" and "the" mean "one or more" unless expressly specified otherwise.

It should also be noted that the terms "coupled" or "coupling" as used herein can have several different meanings depending in the context in which these terms are used. For example, the terms coupled or coupling can have a mechanical or electrical connotation. For example, as used herein, the terms coupled or coupling can indicate that two elements or devices can be directly connected to one another or connected to one another through one or more intermediate elements or devices via an electrical element or electrical signal (either wired or wireless) or a mechanical element depending on the particular context.

Further, although processes, methods, and the like may be described (in the disclosure and/or in the claims) having acts in a certain order, such processes and methods may be configured to work in alternate orders while still having utility. In other words, any sequence or order of actions that may be described does not necessarily indicate a requirement that the acts be performed in that order. The acts of processes and methods described herein may be performed in any order that is practical and has utility. Further, some actions may be performed simultaneously, if possible, while others may be optional, if possible.

When a single device or article is described herein, it may be possible that more than one device/article (whether or not they cooperate) may be used in place of a single device/article. Similarly, where more than one device or article is described herein (whether or not they cooperate), it may be possible that a single device/article may be used in place of the more than one device or article.

As used herein, the wording "and/or" is intended to represent an inclusive-or. That is, "X and/or Y" is intended to mean X or Y or both, for example. As a further example, "X, Y, and/or Z" is intended to mean X or Y or Z or any combination thereof.

It should be noted that terms of degree such as "substantially", "about" and "approximately" as used herein mean a reasonable amount of deviation of the modified term such that the end result is not significantly changed. These terms of degree may also be construed as including a deviation of the modified term, such as by 1%, 2%, 5% or 10%, for example, if this deviation would not negate the meaning of the term it modifies.

Furthermore, the recitation of numerical ranges by endpoints herein includes all numbers and fractions subsumed within that range (e.g. 1 to 5 includes 1, 1.5, 2, 2.75, 3, 3.90, 4, and 5). It is also to be understood that all numbers and fractions thereof are presumed to be modified by the term "about" which means a variation of up to a certain amount of the number to which reference is being made if the end result is not significantly changed, such as 1%, 2%, 5%, or 10%, for example.

The example embodiments of the devices, systems or methods described in accordance with the teachings herein may be implemented as a combination of hardware and software. For example, the embodiments described herein may be implemented, at least in part, by using one or more computer programs, executing on one or more programmable devices comprising at least one processing element and at least one storage element (i.e. at least one volatile memory element and at least one non-volatile memory element). The hardware may comprise one or more input devices and one or more output devices as provided by the various embodiments described herein.

It should also be noted that there may be some elements that are used to implement at least part of the embodiments described herein that may be implemented via software that is written in a high-level procedural language such as object oriented programming. The program code may be written in C, C++ or any other suitable programming language and may comprise modules or classes, as is known to those skilled in object oriented programming. Alternatively, or in addition thereto, some of these elements implemented via software may be written in assembly language, machine language or firmware as needed. In either case, the language may be a compiled or interpreted language.

At least some of these software programs may be stored on a computer readable medium such as, but not limited to, a ROM, a magnetic disk, an optical disc, a USB key and the like that is readable by a device having a processor, an operating system and the associated hardware and software that is necessary to implement the functionality of at least one of the embodiments described herein. The software program code, when read by the device, configures the device to operate in a new, specific and predefined manner in order to perform at least one of the methods described herein.

Furthermore, at least some of the programs associated with the devices, systems and methods of the embodiments described herein may be capable of being distributed in a computer program product comprising a computer readable medium that bears computer usable instructions, such as program code, for one or more processing units. The medium may be provided in various forms, including non-transitory forms such as, but not limited to, one or more diskettes, compact disks, tapes, chips, and magnetic and electronic storage. In alternative embodiments, the medium may be transitory in nature such as, but not limited to, wire-line transmissions, satellite transmissions, internet transmissions (e.g. downloads), media, digital and analog signals, and the like. The computer usable instructions may also be in various formats, including compiled and non-compiled code.

Referring now to FIG. 1, shown therein is a diagram of an example embodiment of an assistive device 10 that can interact with at least one electronic device 30. The assistive device 10 can operate as an interface between physical interfaces and one or more of the electronic devices 30. The assistive device 10 can relay input signals, such as switch input events, from physical interfaces to one or more of the electronic devices 30. Physical interfaces can be external physical interfaces 20, which are external to the assistive device 10, or internal physical interfaces 20, which are internal to or built-in the assistive device 10.

In at least one embodiment, the assistive device 10 can include a peripheral port to receive an input signal from an external physical interface 20. In at least one embodiment, the assistive device 10 can include a plurality of peripheral ports for receiving input signals from a plurality of external physical interfaces 20. For simplicity, a peripheral port is described, although the concepts described herein may be performed using one or more peripheral ports.

Example peripheral ports can include switch ports and/or a wheelchair ports. In some embodiments, a switch port can be a 3.5 mm port in accordance with Simple Electrical Transducer (SET) Standards. When the peripheral port is a switch port, the external physical interface 20 is a switch and the assistive device 10 can receive an input signal representing press and/or release events. In some embodiments, the wheelchair port can provide inputs from a joystick and/or a head array. Joysticks can provide either a binary input in accordance with SET Standards, or a proportional input in accordance with a BLE characteristic. The BLE characteristic can be a standard characteristic, such as a "Human Interface Device", or a custom and extendable characteristic.

The at least one electronic device 30 can include, but is not limited to, a smartphone, a tablet, a personal computer, a television, a gaming console, a cable box, or any other computing device capable of wireless communication. The at least one electronic device 30 can also be an internet-enabled appliance such as, but not limited to, a thermostat, smart lighting, a washer, a dryer, an oven, a dishwasher, a refrigerator, a microwave, a coffee maker, and other small kitchen appliances. The at least one electronic device 30 can also include wired, switch-enabled devices such as a call bell, a garage door opener, a bed tilt mechanism, or a wheelchair tilt mechanism. In at least one embodiment, the peripheral ports can also enable communication from the assistive device 10 to wired electronic devices 30. The electronic devices 30 can be locally connectable or remotely connectable to the assistive device 10. Locally connectable electronic devices refers to electronic devices 30 that are in proximity to the assistive device 10 and that the assistive device 10 can electronically communicate with directly without having to relay messages through another device or network. For instance, smartphones, tables, personal computers, and televisions equipped with Bluetooth® or near field communication antennas, or call bells, garage door openers, bed tilt controllers, and wheelchair tilt controllers that are wired to the assistive device 10 can be locally connectable.

Electronic devices that are remotely connectable includes electronic devices 30 that the assistive device 10 can electronically communicate with indirectly, such as through a server or another device or network. For instance, internet-enabled appliances can be remotely connectable. In some instances, an electronic device 30 can be both locally and remotely connectable. Generally, local connectivity is preferable as it can reduce latency between the time when a message is sent and a corresponding action is performed.

Figure 2:
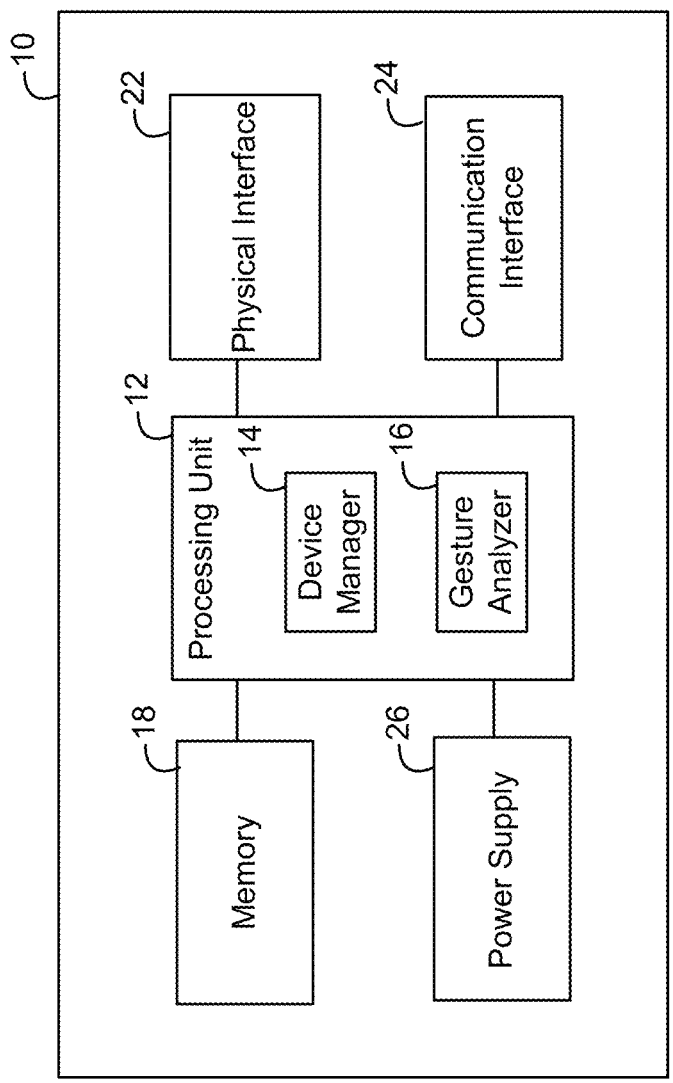
FIG. 2 shows a diagram of an example embodiment of components of an assistive device in accordance with the teachings herein.

Referring now to FIG. 2, shown therein is an example embodiment of components of an assistive device 10. The assistive device 10 can include at least one processing unit 12, memory 18, at least one physical interface 22, at least one communication interface 24, and a power supply 26.

The at least one processing unit 12 can control the overall operation of the assistive device 10. The at least one processing unit 12 can be one or more processors that have enough computing power to provide the various functions of the assistive device 10. For simplicity, a single processing unit 12 is described, although the concepts described herein may be performed using one or more processing units.

The processing unit 12 can be a microcontroller or any like device that has a processing core, memory, and input and output peripherals. For example, in alternative embodiments, a field programmable gate array, an Application Specific Integrated Circuit, a peripheral interface controller, or other specialized circuitry may be used to implement the processing unit 12. The processing unit 12 can further include an Analog to Digital converter and a Digital to Analog converter. The processing unit 12 can further include an internal timer.

Memory 18 can store computer programs that are executable by the processing unit 12 (e.g. using the memory) to operate the assistive device 10. For example, memory 18 can store software modules that are operable by the processing unit 12 for implementing particular control functions.

For example, in at least one embodiment, the memory 18 can include a software module that serves as a device manager 14. The device manager 14 can maintain a list of electronic devices 30 to which the assistive device 10 can connect to, herein referred to as a whitelist. The operation of the device manager 14 is described in more detail below.

In another example, in at least one embodiment, the memory 18 can store a gesture-to-command map. Input signals from the physical interface 20 can represent various gestures. A gesture is generally any sequence of events produced by manipulation of physical interface 20. Gestures can range from a single click (i.e., a switch press followed quickly followed by a switch release) to a sequence of coordinates in a plane (i.e., tracing a shaper or a letter on a track pad).

The gesture-to-command map can be used to determine a command based on a gesture that is represented in a given input signal. Furthermore, the gesture-to-command map can be configured, or customized for a particular user. In at least one embodiment, the memory 18 can include a software module that serves as a gesture analyzer 16 that determines a command based on a given input signal. In other embodiments, the gesture analyzer 16 may be implemented using hardware. The operation of the gesture analyzer 16 is described in more detail below.

The assistive device 10 can include at least one communication interface 24 for communicating with the at least one electronic device 30. The at least one communication interface 24 can include a wireless communication interface and/or a wired communication interface. The at least one communication interface 24 can be one or more communication interfaces. For simplicity, a single communication interface 24 is described, although the concepts described herein may be performed using one or more communications interface 24. Furthermore, when a plurality of communication interfaces 24 are provided, a handoff protocol between two communication interfaces can be employed to maintain connectivity. For example, a handoff protocol can be used when Wi-Fi and GSM communication interfaces are included in the assistive device 10.

In at least one embodiment, a wireless communication interface can enable wireless communications according to a Wi-Fi protocol (e.g. using an IEEE 802.11 protocol or similar). In at least one embodiment, the wireless communication interface can include hardware and software for enabling wireless communications with cellular networks such as 2G (GSM), 3G, 4G, or LTE. In at least one embodiment, the wireless communication interface can include additionally or optionally include a short range communication antenna such as near field communication, Bluetooth®, Bluetooth® Low Energy (BLE), ZigBee etc.

In at least one embodiment, a wired communication interface can enable the assistive device 10 to be connected to a wired device. In at least one embodiment, the wired communication interface can be a switch port, such as a 3.5 mm port in accordance with Simple Electrical Transducer (SET) Standards.

In at least one embodiment, the assistive device 10 can include a built-in physical interface 22. In some embodiments, the assistive device 10 can include built-in physical interfaces 22 and/or peripheral ports (not shown in FIG. 2). In at least one embodiment, the built-in physical interface 22 can be a switch. In some embodiments, the switch can be a seesaw switch (described below in reference to FIGS. 3, 4A to 4C).

In at least one embodiment, the built-in physical interface 22 include a touch-sensitive surface and a track pad coupled to the touch-sensitive surface. When an external force is applied to the touch-sensitive surface, the track pad can generate an input signal In at least one embodiment, the assistive device 10 can receive input signals from an external physical interface 20 via the wireless communication interface. That is, in some embodiments, the external physical interface 20 is wireless and the assistive device 10 can receive input signals from wireless communication. For example, in some embodiments, the assistive device 10 can receive input signals from an external physical interface 20 via Bluetooth® Low Energy (BLE).

Example wireless external physical interfaces 20 include a wireless switch providing an input signal of switch press events and/or switch release events, a wireless joystick providing an input signal of binary inputs, a wireless joystick providing a proportional input signal; all of these wireless signals being transmitted in accordance with either a standard, pre-defined BLE characteristic (such as "Human Interface Device") or a custom and extendable Bluetooth® Low Energy (BLE) characteristic.

The custom BLE characteristic currently allows the external physical interface 20 to report switch input states to the assistive device 10, but can be extended to allow for the exchange of additional contextual data relevant and specific to the interaction between the assistive device 10 and the external physical interface 20.

Examples of data that can be exchanged between the assistive device 10 and the external physical interface 20 include a battery charge, a speed, seat pressure, or posture of a user in a wheelchair, when the external physical interface 20 is a wheelchair, and an identifier for the external physical interface 20 itself.

In at least one embodiment, the assistive device 10 can include a power supply 26 to provide power to various circuit components of the assistive device 10. In some embodiments, the power supply 26 can include an electrical energy storage component (not shown). In at least one embodiment, power supply 26 can also include a sliding switch to power the assistive device 10 on and off.

In some embodiments, the electrical energy storage component is a battery. The electrical energy storage component can be rechargeable by a wireless or wired mechanism. The electrical energy storage component can have an effective discharge cycle that enables the user to use the assistive device 10 for a certain number of hours without recharging. For example, the electrical energy storage component can have a discharge cycle of about 48 hours with continuous use.

In at least one embodiment, the assistive device 10 can also include sensors (not shown in FIG. 2). Sensors can include location sensors (e.g., GPS), motion sensors, ambient light sensors, and temperature sensors. The sensors can generate monitoring data about the user and/or the user's environment. The monitoring data can, in turn, be transmitted to a remote server, which a user's trusted caregiver may access in order to monitor the user. In addition, such monitoring data can be analyzed in order to generate an alert to caregivers under certain conditions. For instance, alerts may be related to a user's location being in an unsafe area and/or a temperature of the user being too high or too low.

In at least one embodiment, the assistive device 10 can also include an output indicator (not shown in FIG. 2). An output indicator, such as a light source or a light emitting diode (LED) for example, can provide visual feedback. The LED can receive a device status signal from the processing unit 12 and provide visual indication of the device status. Alternatively, or in addition thereto, the output indicator can be a speaker or a buzzer, for example, that is used to provide audio feedback. Similar to the LED, a speaker or buzzer can receive a device status signal from the processing unit 12 and provide audio indication of the device status.

In some embodiments, different device statuses can be indicated by the light source displaying different colors or the speaker emitting different sounds. In some embodiments, the device status may relate to the assistive device 10 being powered on. For example, a visual indicator can be provided when the assistive device 10 is powered on. In another example, a visual indicator can be provided when the assistive device 10 seeks to establish an electronic communication connection to one of the electronic devices 30. In some embodiments, the device status may relate to alerts generated from monitoring data described above. For example, an audio indicator can be provided for an alert based on the monitoring data indicating a certain condition.

In another example, an audio indicator can be provided when a particular electronic device 30 is selected.

Figure 3:
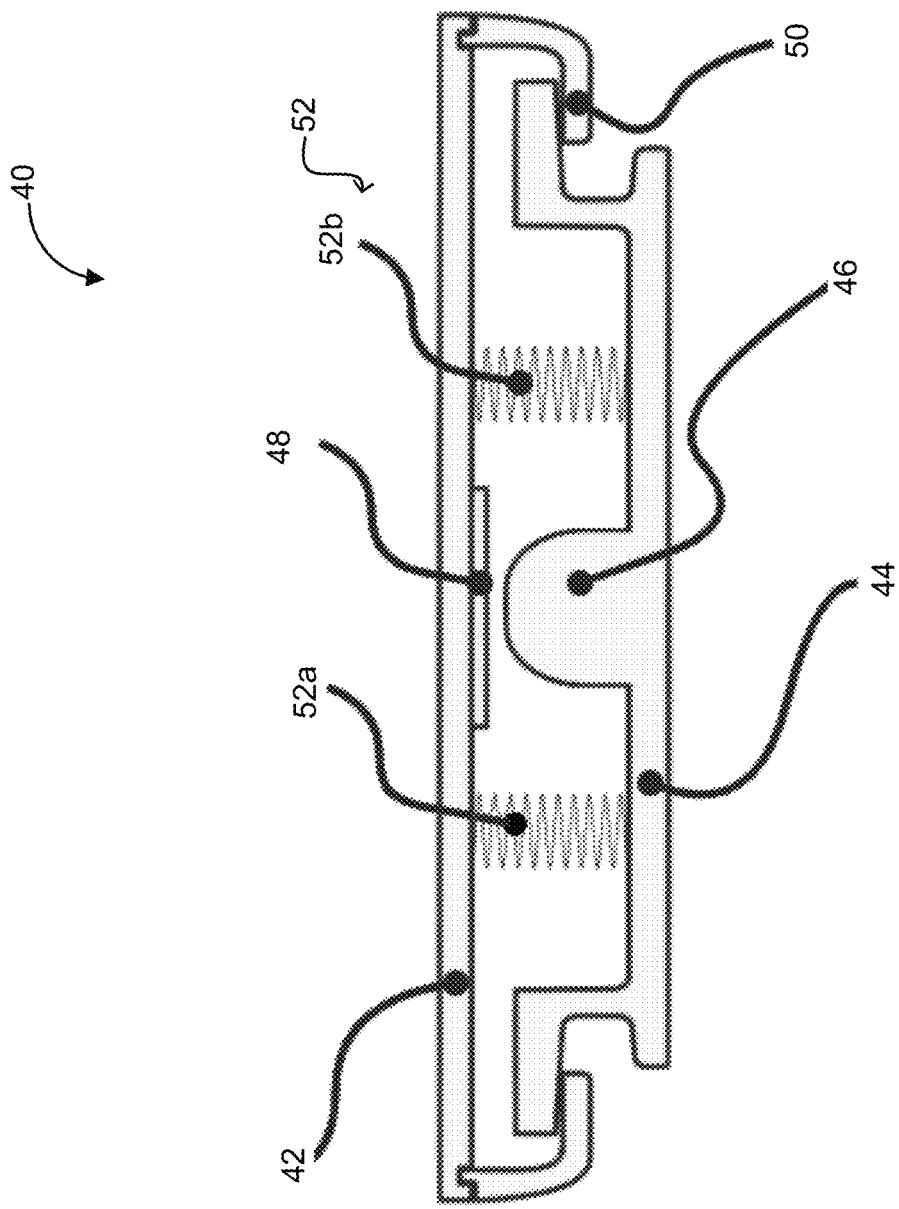
FIG. 3 shows a cross-sectional profile view of an example embodiment of a built-in see-saw switch that can be used in an assistive device.

Referring now to FIG. 3, shown therein is a profile view of a seesaw switch 40. The seesaw switch 40 includes a cover 42, a base 44, and a plurality of compression spring members 52 (as shown in FIG. 2, the compression spring members 52a and 52b may be collectively referred to as the compression spring members 52).

Each of the cover 42 and the base 44 can move independently of each other. The independent movement of the cover 42 and the base 44 allows the cover 42 to be releasably depressable. The cover 42 can be suspended over the base 44 using compression spring members 52. The cover 42 has cover hooks 50 that engage with flanged regions of the base 44. The flanged regions of the base 44 apply a constant downward force (e.g., in a direction towards the base 44) on the cover hooks 50 due to the biasing provided by the compression spring members 52 in their normal resting position which have a sufficient length to keep the base 44 spaced apart from the cover 42 so that the cover hooks 50 and the flanged regions of the base 44 engage one another. Thus, the cover hooks 54 prevent the detachment of the cover 42 and the base 44. In some embodiments, the constant downward force can be provided by another coupling mechanism such as a latch or fastener rather than the compression spring members 52.

In addition, compression spring members 52 positioned between the cover 42 and the base 44 can apply a constant upward force (e.g., in a direction away from the base 44) on the cover 42. Thus, the compression spring members 52 create a gap between the cover 42 and the base 44. In some embodiments, the constant upward force can be provided by another biasing mechanism. For simplicity, two compression spring members 52 are described and illustrated, although the concepts described herein may be performed using one, two, or more than two compression spring members.

Each of the cover 42 and base 44 can have a switch activation surface. On the cover 42, the switch activation surface 48 can be mounted to an inner surface of the cover 42. On the base 44, the switch activation surface can be located on a plunger 46, which is a protrusion or boss that extends away from an inner surface of the base 44. In some embodiments, the switch activation surface 48 can be an electromechanical membrane switch. In some embodiments, the switch activation surface 48 can be a force-sensitive piezoelectric element. The switch activation surface 48 and the plunger 46 can be aligned, or face one another, to permit physical contact of one another when the switch 40 is depressed. When the switch activation surface 48 and the plunger 46 are in physical contact with one another, the switch 40 can generate an input signal.

Figure 4A:
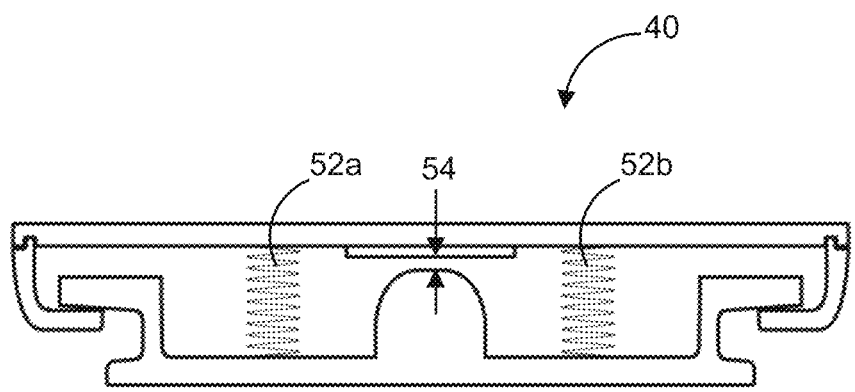
FIGS. 4A-4C show profile views of an example embodiment of the built-in see-saw switch of FIG. 3 in a non-depressed state, a depressed state, and one-sided depressed state.
Figure 4B:
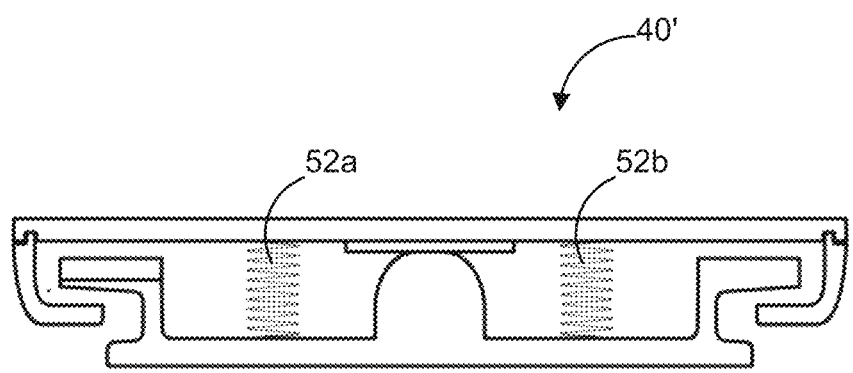
Figure 4C:
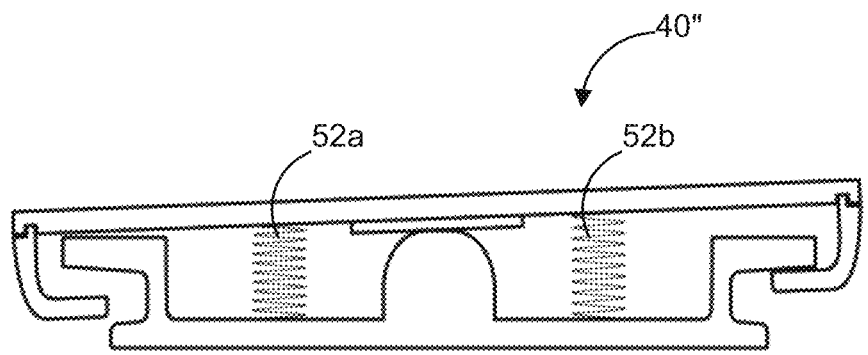

Referring now to FIGS. 4A to 4C, shown therein are various cross-sectional profile views of the seesaw switch 40 in various states.

In FIG. 4A, the seesaw switch 40 in a non-depressed or resting state is illustrated. That is, when no external force is applied to the outer surface of the cover 42. As described above, the compression spring members 52 create a gap between the cover 42 and the base 44. The compression spring members 52 apply an upward force, causing the switch activation surface 48 to be located at a first height with respect to the base 44 that is higher than the height of the plunger 46 with respect to the base 44. More specifically, the compression spring members 52a and 52b, when not compressed, cause the cover 42 to be located at a height that is higher than a plane orthogonal to a top of the plunger 46.

As a result, a gap 54 is created between the plunger 46 and the switch activation surface 48 when no external forces are applied to the surface of the switch 40.

In FIG. 4B, the seesaw switch 40 in a fully depressed state 40' is illustrated. That is, when an external force is applied in a generally downward direction to the entire surface of the cover 42, or to the cover 42 in an area coincident with the plunger 46. Both of the compression spring members 52a and 52b are compressed by the applied external force, permitting the switch activation surface 48 to contact the plunger 46. More specifically, the compression spring members 52a and 52b are compressed and allow the cover 42 to move toward the plunger 46 and be located at the plane orthogonal to the top of the plunger 46. As a result, the plunger 46 and the switch activation surface 48 come into contact when the external force is applied to the surface of the cover 42 of the switch 40 and is large enough to overcome the resting biasing force provided by the compression spring members 52a and 52b.

In FIG. 4C, the seesaw switch 40 in a partially depressed state 40" is illustrated. That is, when an external force is applied in a generally downward direction to a portion of the exterior surface of the cover 42, or an area not-coincident with the plunger 46. Only the compression spring member 52a is compressed by the applied force while the compression spring member 52b remains uncompressed. Since the compression spring members 52a and 52b are located on either side of the plunger 46, compression of only one compression spring members 52a and 52b still permits the switch activation surface 48 to contact the plunger 46, similar to the fully depressed state 40' of FIG. 4B. With the seesaw switch 40, an external force at any point on the surface of the cover 42 can cause physical contact between the plunger 46 and the switch activation surface 48.

Figure 5:
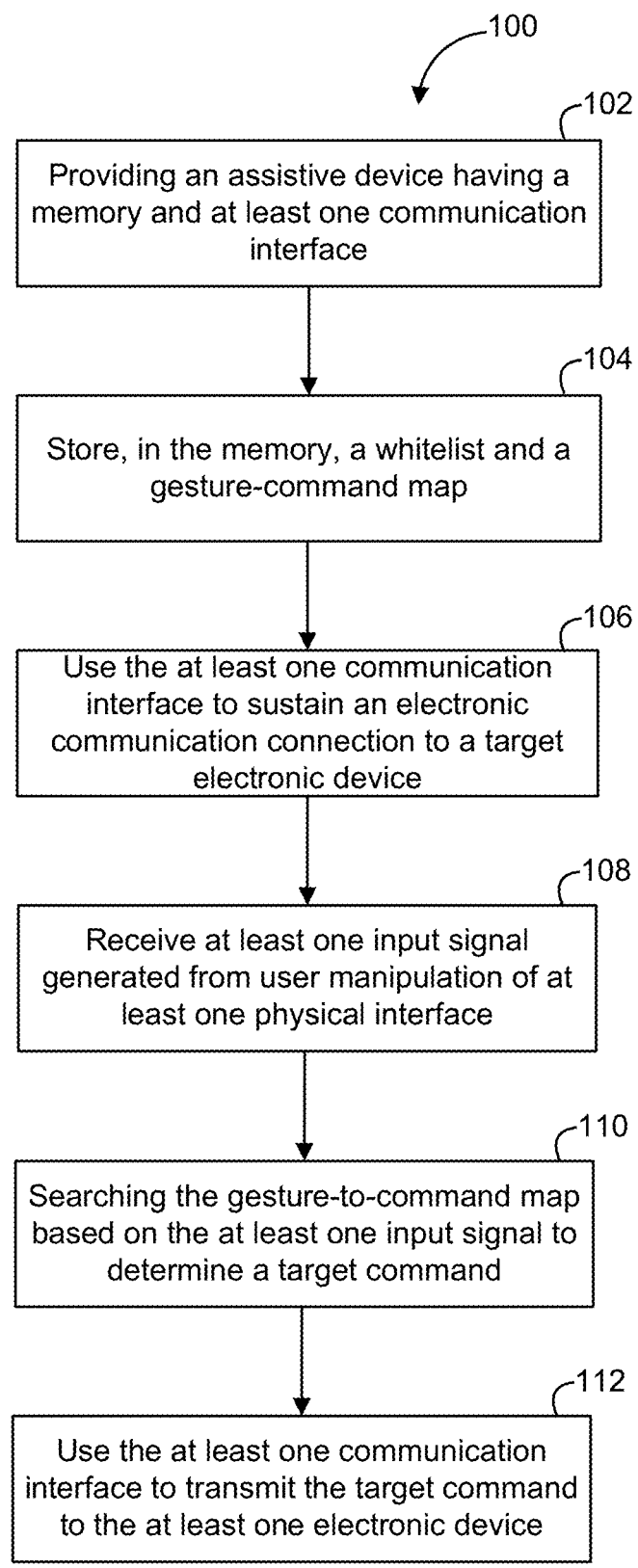
FIG. 5 shows a flowchart of an example embodiment of a method of using an assistive device to interact with at least one electronic device in accordance with the teachings herein.

Referring now to FIG. 5, shown therein is a flowchart of an example embodiment of a method 100 of using an assistive device to interact with at least one electronic device 30 in accordance with the teachings herein.

The method 100 begins at step 102 with providing an assistive device 10 having a memory 18 and at least one communication interface 24.

At step 104, a whitelist of the at least one electronic device 30 that can be interfaced with the assistance device 10 and a gesture-to-command map comprising a plurality of input signals that represent gestures can be provided by the physical interface 20, where the input signals represent gestures that can be used with the at least one electronic device 30, can be stored in memory 18. In some embodiments, a device manager 14 can store and maintain the whitelist. In some embodiments, a gesture analyzer 16 can store and maintain the gesture-to-command map.

The whitelist can be used to identify electronic devices 30 that the assistive device 10 can connect to. The use of the whitelist enables the assistive device 10 to be initially configured to operate with one of the electronic devices 30, followed by continued interaction with one or more of the electronic devices 30 as long as the electronic devices 30 remain on the whitelist. Hence, the assistive device 10 can connect to a plurality of electronic devices 30 without reconfiguring a switch interface each time the user wishes to control a different electronic device 30. That is, users can successively control a different electronic device 30 on the whitelist without reconfiguring a switch interface each time the user wishes to control a different electronic device 30.

In at least one embodiment, access to an electronic device 30 on the whitelist can be individually targeted. That is, a control command can be directed to a specific electronic device 30. For example, in at least one embodiment, electronic devices 30 on the whitelist can be accessed in a particular sequence. That is, the assistive device 10 can navigate the whitelist to access each electronic device 30 in sequence or to skip through some of the electronic devices 30 in the sequence until the desired electronic device 30 is selected. Once an electronic device 30 on the whitelist is selected, or navigated to, commands from the assistive device 10 can be relayed to the selected, or target electronic device 30.

The device manager 14 can be implemented using software and/or hardware. In some embodiments, when the device manager 14 is implemented using software, the device manager 14 can be implemented using the C programming language toolchain, for example.

In some embodiments, a handshaking process between the assistive device 10 and an electronic device 30 is used in order to add and/or remove an electronic device 30 from the whitelist. In the handshaking process, each of the electronic device 30 and the assistive device 10 transmit a self-identification that is received by the other. The self-identification can be implemented wirelessly using the standard or custom Bluetooth® Low Energy characteristics, which are defined in Bluetooth® Low Energy standards. The self-identification can be implemented for wired connections using a packet-based protocol.

The whitelist can include a locally connectable electronic device 30. In order to add a locally connectable electronic device 30 to the whitelist, the assistive device 10 is first paired with the electronic device 30, in accordance with the pairing process of the communication technology that is used by the locally connectable electronic device 30 for communication (e.g., Bluetooth®). After the assistive device 10 and the locally connectable electronic device 30 are successfully paired, the locally connectable electronic device 30 can be added to the whitelist. Locally connectable electronic devices include both wireless electronic devices and wired electronic devices, including wired, switch-enabled electronic devices.

The whitelist can include a remotely connectable electronic device 30. In order to add a remotely connectable electronic device 30 to the whitelist, the assistive device 10 may be required to provide authentication information to a device management server that controls access to that particular remotely connectable electronic device. When the assistive device 10 provides correct authentication information to the device management server, the device management server then recognizes the assistive device 10 as being an authorized user that can control the remotely connectable electronic device 30. After the device management server recognizes the assistive device 10 as an authorized device, the remotely connectable electronic device can be added to the whitelist.

Use of the whitelist can enable users to control multiple electronic devices 30, irrespective of the platform, make and/or architecture of the electronic device 30. That is, management of the electronic communication connection by the assistive device 10 with one or more of the electronic devices 30 allows the assistive device 10 to be agnostic in respect of the electronic device 30 platform. Because the assistive device 10 manages the communication connection to each of the one or more electronic devices 30, there is no requirement for the electronic devices 30 to communicate with one another. That is, the electronic devices 30 do not need to share the same platform.

In addition, use of a stored whitelist allows the assistive device 10 to locally manage the electronic communication connections since it is not required for the assistive device 10 to access a remote computer in order to obtain information that is in the whitelist. Local management of electronic communication connections can reduce delays that could otherwise arise from network delays.

After an electronic device 30 is added to the whitelist, further configuration from the assistive device 10 may be required in order for the assistive device 10 to interact with the electronic device 30. In some embodiments, the whitelist can also store information on how commands are transmitted to a given electronic device 10. For example, for locally connectable wireless electronic devices, the whitelist can specify a particular type of electronic communication connection and/or a particular type of data transmission protocol for a given electronic device 10. For example, the whitelist can specify for a personal computing device, such as a tablet, that the electronic communication connection can be established via BLE and that data can be sent using the custom BLE characteristic.

In some embodiments, the whitelist can store information about the requirements for the electronic communication connection to a given electronic device 10, in order for the assistive device 10 to manage, that is establish and maintain, the electronic communication connection. For example, some electronic devices 30 can enter power-saving states after periods of inactivity. The whitelist can store information about how to prevent entry into such power-saving states if desired. For locally connectable wired electronic devices 30, the whitelist can store information about a physical relay of the assistive device 10 to be activated in order to command the electronic device 30.

For remotely connectable electronic devices, the whitelist can store an address for an appropriate server, such as the central server or the device management server, and/or content that messages to that server must include. In some embodiments, the central server can store information about the transmission of received commands to additional servers, namely a device management server or a third-party server. In this case, it can be said that the central server stores a portion of the whitelist. For example, the whitelist can store information about sending notifications to third-party services to alert them that commands have been transmitted.

In some embodiments, the whitelist can store information about the requirements for the electronic communication connection to a server. For example, a connection to a server may be terminated after a period of inactivity. The whitelist can store information about how to prevent termination of the connection, if desired. For example, the assistive device 10 can transmit pings over MQTT to sustain a connection with the central server.

The gesture-to-command map is a listing of commands that can be used with the electronic devices 30. An input signal representing a gesture that can be received at a physical device 20 can be assigned to each command. The plurality of commands can include at least one selection command and at least one control command. The term selection command used herein refers to a command that allows the assistive device 10 to navigate through the whitelist. The term control command used herein refers to switch input events that are relayed to the electronic devices 30 to control the operation of the electronic device 30. The use of a single gesture-to-command map containing both selection commands and control commands allows a single physical interface to be used simultaneously for the purpose of selecting electronic devices 30 and controlling the selected electronic device 30, in accordance with the teachings herein.

Furthermore, with the use of a gesture-to-command map, the particular gestures used for selecting and controlling devices can be customized for each user. The assistive device 10 can include a default gesture-to-command map. In at least one embodiment, users can change the default command to another command that better suits their needs.

Each individual with physical impairments can have different abilities. The default gesture-to-command map can be configured, or customized for a particular user having certain abilities. For example, in at least one embodiment, an input signal representing a three-second activation of a physical interface 20 can be configured for a first user as a selection command. For a second user, an input signal representing a six-second activation of a physical interface 20 can relate to the same selection command.

Furthermore, gestures can be customized to be specific to a particular device. For example, when the assistive device 10 is selected to control a particular device, a given gesture, such as a single press, can be related to a first control command for the particular device. However, when the assistive device 10 is selected to control a different electronic device 30, the same gesture (i.e., the single press) can relate to a second control command on the second electronic device 30 that is different from the first control command on the first electronic device 30.

In some embodiments, additional gestures can include a single press followed by a release, a long press (i.e., three-second), a double click, a triple click, consecutive holds (i.e., six-seconds), and/or any other synchronous or asynchronous switch input event sequences. In some embodiments wherein the physical interface is a joystick, track pad, or pointing device, the gesture can be the drawing of a letter. Each of these gestures can be stored in the gesture-to-command map in relation to a particular command.

Configuration of the gesture-to-command map can be performed using a software application operating on the central server. The software application can collect all the information necessary to implement the gesture-to-command map and transmit the information to the assistive device 10 via the BLE characteristics, which may be standard characteristics or custom and extendable characteristics. The assistive device 10 may store a default gesture-to-command map and update the default gesture-to-command map with the information received form the central server.

In some embodiments, control commands can be keyboard events, such 10 standard function keys for 'F1' to 'F10'. Keyboard events can be used for controlling personal electronic devices and/or apps (i.e., Android®, iOS®, Windows®, OSX®, AppleTV®). In some embodiments, control commands can be any be configurable keyboard event, namely any universal serial bus (USB) Human Interface Device (HID) codes. Configurable keyboard events can also be used for controlling personal electronic devices and/or apps. In some embodiments, control commands can be MQTT (MQ Telemetry transport) or HTTP calls. In some embodiments, control commands can be dry contact switch output (relays) for controlling wired electronic devices. In some embodiments, control commands can be a proportional joystick or pointing device output for controlling the same.

In some embodiments, the gesture-to-command map can include a series of binary flags, each binary flag can be associated with a gesture. If a gesture is related to a control command involving a third-party integration server, the binary flags can be identified as such. During operation of the assistive device 10, when a gesture related to a control command involving a third-party integration server is received, the switch event can be transmitted to the central server. At the central server, sending notification to the third-party service is transmitted to alert them of the switch event. That is, a trigger for the third-party integration server is populated with the user's data and configuration. In addition, the event is made available to the third-party server, which is eventually transmitted to the device management server.

In some embodiments, the gesture-to-command map can include an identifier, such as a key-value pair in which the key relates to the gesture and the value relates to the command. The identifiers can be stored in association with control commands involving a third-party integration server. Use of an identifier instead of a binary flag allows commands for a plurality of third-party integration services to be defined.

In at least one embodiment, the whitelist can be navigated as a circular loop. For instance, a selection command can be defined to be a "next" command or a "previous" command, which will each navigate to the next successive electronic device 30 on the whitelist or the previous electronic device 30 on the whitelist, respectively. In at least one embodiment, a particular electronic device 30 can be marked as a "home" device (i.e., "favorite" device that is used most often) and a "home" selection command can be used to select that "home" device.

At step 106, the at least one communication interface 24 can be used to sustain an electronic communication connection to a target electronic device 30. Some electronic devices 30 require an "always on" connection in order to receive and act on a control command. For instance, current smart phones, tablets, and personal computers do not act on control commands when they are in a "standby" or "hibernate" state. In contrast, some electronic devices 30 do not require an "always on" connection in order to receive and act on a control command. For example, wired and Internet-enabled appliances can receive and act on control commands at any time.

For electronic devices 30 that require an "always on" connection, a delay can occur if a user must wait until the target electronic device is "on" or that a connection must be re-established, before transmitting a control command. In order to reduce such delays, the assistive device 10 can transmit an innocuous command to the electronic device 30. Innocuous commands can be commands that do not cause the electronic device to take undesired action. However, they are sent in order to maintain an "on" connection and prevent the electronic device 30 from switching to another a power saving state such as "standby" or "hibernate".

The innocuous command can be transmitted before a predefined idle time duration has elapsed which otherwise causes the electronic device 30 to change states had the innocuous command not been transmitted. In at least one example embodiment, the innocuous command can relate to the depression the "SHIFT" key. The "SHIFT" key does not cause the electronic device 30 to take any undesired action and also ensures that the electronic device 30 remains "on".

The frequency at which innocuous commands are transmitted to a particular electronic device 30 can depend on information stored in the whitelist. In particular, as described above, the whitelist can store information relating to the requirements for the electronic communication connection to a given electronic device 10. In this example, the whitelist can store a pre-specified time duration of inactivity that triggers the electronic device 30 to enter a power saving state.

At step 108, the assistive device 10 can receive at least one input signal generated from user manipulation of at least one physical interface. As described above, the at least one physical interface 22 can be a built-in physical interface, such as a built in switch, such as the see saw switch 40, for example, or an external physical interface 20. Furthermore, in some embodiments, the external physical interface 20 can be coupled to the assistive device 10 via a wired connection and a peripheral port. In some embodiments, the external physical interface 20 can be coupled to the assistive device 10 via a wireless connection and a wireless communication interface.

In some embodiments, input signals can be received from multiple physical interfaces including a built-in physical interface and an external physical interface. In at least one embodiment, switch de-bouncing can be implemented to avoid multiple simultaneous activations or input signals. That is, upon the arrival of a completed input signal (i.e., a press-and-release event), the processing unit 12 can disregard any additional input signals for a pre-determined time window after receiving the completed input signal. In some embodiments, the pre-determined time window is approximately 20 milliseconds, for example, but other time periods may be used in some embodiments.

At step 110, the gesture-to-command map can be searched based on the at least one input signal to determine when a target command has been provided by the user of the assistive device 10. In some embodiments, the gesture analyzer 16 determines a target command based on a given input signal. In particular, the gesture analyzer 16 can identify an input signal stored in the gesture-to-command map that the given input signal that was just received matches, or is most similar to. The gesture analyzer 16 can determine that the target command for a given input signal is the command stored in association with the most similar, or closest input signal match of the given input signal. In some embodiments, the target command can be a selection command. That is, the target command can relate to navigating the whitelist.

In some embodiments, the target command can be a control command. Furthermore, in some embodiments, a control command can be a device-specific control command. Device-specific control commands can be issued to wired electronic device 30 or wireless electronic devices 30 that do not require an "always on" connection. That is, device-specific control commands can be transmitted to the corresponding electronic device 30 at any time, irrespective of the current target electronic device selection. When the gesture analyzer 16 determines that the target command is a device-specific control command, the gesture analyzer 16 also determines the target electronic device associated with the device-specific control command by using the whitelist.

In contrast, a control command can also be a generic control command. Generic control commands can be issued to an electronic device 30 that the assistive device 10 is currently selected to. That is, generic control commands can be transmitted to the electronic device 30 that is the current target electronic device selection. Generally, generic control commands are issued to electronic devices 30 that require an "always on" connection. As described above, generic control commands can also be device specific.

Once the target command is determined, the method proceeds to transmitting the target command to the at least one electronic device 30 using the at least one communication interface 24 at step 112.

At step 112, when the target command is a selection command, the assistive device 10 can establish and sustain an electronic communication connection to a second or another target electronic device from the whitelist where the current electronic device that the assistive device 10 is interfaced with can be considered a first target electronic device from the whitelist. In some embodiments, the assistive device 10 can transmit the selection command in order to establish the electronic communication connection to a particular target electronic device that the user of the assistive device 10 is trying to select. As described above, according to some embodiments, the selection command can relate to navigation of the whitelist and accordingly, the second target electronic device can be the "next" electronic device 30 on the whitelist.

In at least one embodiment, the assistive device 10 can sustain electronic communication connections to only one electronic device 30 at a time. That is, the assistive device 10 can transmit innocuous commands to one electronic device 30 at time. Accordingly, upon establishing an electronic communication connection to a second target electronic device, the assistive device 10 may discontinue sustaining the electronic communication connection to the first target electronic device, that is the target electronic device prior to the current selection command. Alternatively, in at least one embodiment, the assistive device 10 is not limited to only one electronic communication connection and can transmit innocuous commands to multiple electronic devices 30 at a time.

At step 112, when the target command is a device-specific control command, the assistive device 10 can use the at least one communication interface 24 to transmit the device-specific command to the at least one electronic device 30 that is the current target device. With device-specific control commands, a user of the assistive device 10 can control different electronic devices simultaneously. For instance, the assistive device 10 can be selected to control a smartphone. A control command can be sent to the smartphone, and can then be immediately followed by a device-specific control command that is sent to a thermostat without the need for a separate step of first selecting the thermostat for control.

When the target command is a generic control command at step 112, the assistive device 10 can use the at least one communication interface 24 to transmit the generic control command to the current target electronic device 30. Prior to transmitting the generic control command to the current target electronic device 30, the assistive device 10 will have established and sustained an electronic communication connection with the current target electronic device 30 (e.g., the current selected device).

When the target electronic device 30 is a locally connectable electronic device, the target command can be transmitted directly from the assistive device 10 to the target electronic device 30. In some embodiments, direct transmission can be achieved using near field communications, for example.

When the target electronic device 30 is a remotely connectable electronic device, the target command can be transmitted indirectly from the assistive device 10 to the target electronic device 30. In some embodiments, indirect transmission can be achieved by transmitting the target command to any appropriate server, which in turn, transmits the target command to the target electronic device. In some embodiments, indirect transmission can be routed through a central server supporting the assistive device 10. Alternatively, or in addition thereto, in some embodiments, indirect transmission can also be routed through a device management server provided by the electronic device manufacturer. In yet another alternative or in addition thereto, in some embodiments, indirect transmission can also be routed through a third-party integration service, such as If This Then That (IFTTT)®, Logitech's Harmony®, or Amazon's Alexa®.

In some embodiments, the method 100 can further involve the assistive device 10 waiting to receive a confirmation from the electronic device 30 of the transmitted command. When confirmation is not received, the assistive device 10 can determine that the electronic device 30 is not responsive to the transmitted command and that the electronic communication connection has failed. In at least one embodiment, re-establishing the connection can be attempted for a pre-specified duration of time. For example, in some embodiments, the assistive device 10 can attempt to re-establish the connection for about 30 seconds.

If the connection cannot be re-established within a certain pre-specified duration of time, the assistive device 10 can automatically attempt to establish a connection with another electronic device 30 on the whitelist. Preferably, re-establishing a connection with the failed electronic device or with another electronic device does not require input (i.e., manipulation) by the user. The automatic connection recovery following a loss of an electronic communication connection can be convenient for users with physical impairments who cannot easily manipulate a physical interface.

Numerous specific details are set forth herein in order to provide a thorough understanding of the example embodiments described herein. However, it will be understood by those of ordinary skill in the art that these embodiments may be practiced without these specific details. In other instances, well-known methods, procedures and components have not been described in detail so as not to obscure the description of the embodiments. Furthermore, this description is not to be considered as limiting the scope of these embodiments in any way, but rather as merely describing the implementation of these various embodiments.

The invention claimed is:

1. An assistive device for interacting with at least one electronic device, the assistive device comprising:
   at least one communication interface;
   a memory to store:
      a whitelist having a list including the at least one electronic device; and
      a gesture-to-command map comprising a plurality of input signals, each input signal in linked association with one of a plurality of commands, the plurality of commands comprising at least one selection command and at least one control command; and
   at least one processing unit configured for:
      using the at least one communication interface to sustain an electronic communication connection to a target electronic device that is in the whitelist;
      receiving at least one input signal generated from user manipulation of at least one physical interface;
      searching the gesture-to-command map based on the at least one input signal to determine a target command; and
      using the at least one communication interface to transmit the target command to the at least one electronic device.

2. The assistive device of claim 1, further comprising the at least one physical interface.

3. The assistive device of claim 1, further comprising at least one peripheral port for connecting a physical interface of the at least one physical interface to the assistive device.

4. The assistive device of claim 1, wherein:
   the at least one electronic device comprises at least one locally connectable electronic device; and
   the processing unit is further configured for:
      using the at least one communication interface to pair to the locally connectable electronic device; and
      adding the locally connectable electronic device to the whitelist.

5. The assistive device of claim 1, wherein:
   the at least one electronic device comprises at least one remotely connectable electronic device;
   the processing unit is further configured for:
      providing authentication information to a device management server that is in electronic communication with the remotely connectable electronic device; and
      adding the remotely connectable electronic device to the whitelist.

6. The assistive device of claim 5, wherein when the target electronic device is a remotely connectable electronic device, the at least one communication interface is used to transmit the target command to the target electronic device by transmitting the target command to the device management server.

7. The assistive device of claim 1, the at least one communication interface is used to transmit an innocuous command to the target electronic device in order to sustain the electronic communication connection to the target electronic device.

8. The assistive device of claim 1, wherein the processing unit is further configured to attempt to re-establish the electronic communication to the target electronic device in response to determining that an electronic communication connection to a target electronic device has failed.

9. The assistive device of claim 8, wherein the processing unit is further configured to establish an electronic communication connection to another target electronic device in the whitelist in response to determining that an electronic communication connection to a target electronic device has failed.

10. The assistive device of claim 1, wherein:
   the at least one electronic device comprises at least two electronic devices;
   the target command comprises a selection command;
   the sustaining an electronic communication connection to a target electronic device comprises sustaining an electronic communication connection to a first target electronic device;
   the searching the gesture-to-command map based on the at least one input signal to determine a target command comprises searching the gesture-to-command map to determine that the at least one input signal corresponds to the selection command; and
   the using the at least one communication interface to transmit the target command to the at least one electronic device comprises establishing and sustaining an electronic communication connection to a second target electronic device in the whitelist.

11. The assistive device of claim 1, wherein:
   the at least one electronic device comprises at least two electronic devices;
   the target command comprises a device-specific control command;
   the sustaining an electronic communication connection to a target electronic device comprises sustaining an electronic communication connection to a first target electronic device;

the searching the gesture-to-command map based on the at least one input signal to determine a target command comprises searching the gesture-to-command map to determine that the at least one input signal corresponds to the device-specific control command, the device-specific control command corresponding to a second target electronic device in the whitelist; and the using the at least one communication interface to transmit the target command to the at least one electronic device comprises using the at least one communication interface to transmit the device-specific command to the second target electronic device.

12. The assistive device of claim 1, wherein:
the target command comprises a generic control command;
the sustaining an electronic communication connection to a target electronic device comprises sustaining an electronic communication connection to a first target electronic device;
the searching the gesture-to-command map based on the at least one input signal to determine a target command comprises searching the gesture-to-command map to determine that the at least one input signal corresponds to the generic control command; and
the using the at least one communication interface to transmit the target command to the at least one electronic device comprises using the at least one communication interface to transmit the generic control command to the first target electronic device.

13. The assistive device of claim 1, wherein the gesture-to-command map is configurable by a user.

14. The assistive device of claim 1, wherein the processing unit is further configured for using the at least one communication interface to receive data from the at least one electronic device.

15. A method for interacting with at least one electronic device, the method comprising:
providing an assistive device having a memory and at least one communication interface;
storing, in the memory, a whitelist having a list including the at least one electronic device and a gesture-to-command map comprising a plurality of input signals, each input signal in linked association with one of a plurality of commands, the plurality of commands comprising at least one selection command and a control command;
using the at least one communication interface to sustain an electronic communication connection to a target electronic device that is in the whitelist;
receiving, at the assistive device, at least one input signal generated from user manipulation of at least one physical interface;
searching the gesture-to-command map based on the at least one input signal to determine a target command; and
using the at least one communication interface to transmit the target command to the at least one electronic device.

16. The method of claim 15, wherein:
the at least one electronic device comprises at least one locally connectable electronic device; and
the method further comprises:
using the at least one communication interface to pair to the locally connectable electronic device; and
adding the locally connectable electronic device to the whitelist.

17. The method of claim 15, wherein:
the at least one electronic device comprises at least one remotely connectable electronic device;
the method further comprises:
providing authentication information to a device management server that is in electronic communication with the remotely connectable electronic device; and
adding the remotely connectable electronic device to the whitelist.

18. The method of claim 17, wherein when the target electronic device is a remotely connectable electronic device, the at least one communication interface is used to transmit the target command to the target electronic device by transmitting the target command to the device management server.

19. The method of claim 15, the at least one communication interface is used to transmit an innocuous command to the target electronic device in order to sustain the electronic communication connection to the target electronic device.

20. The method of claim 15, further comprising attempting to re-establish the electronic communication to the target electronic device in response to determining that an electronic communication connection to a target electronic device has failed.

21. The method of claim 20, further comprising establishing an electronic communication connection to another target electronic device in the whitelist in response to determining that an electronic communication connection to a target electronic device has failed.

22. The method of claim 15, wherein:
the at least one electronic device comprises at least two electronic devices;
the target command comprises a selection command;
the sustaining an electronic communication connection to a target electronic device comprises sustaining an electronic communication connection to a first target electronic device;
the searching the gesture-to-command map based on the at least one input signal to determine a target command comprises searching the gesture-to-command map to determine that the at least one input signal corresponds to the selection command; and
the using the at least one communication interface to transmit the target command to the at least one electronic device comprises establishing and sustaining an electronic communication connection to a second target electronic device in the whitelist.

23. The method of claim 15, wherein:
the at least one electronic device comprises at least two electronic devices;
the target command comprises a device-specific control command;
the sustaining an electronic communication connection to a target electronic device comprises sustaining an electronic communication connection to a first target electronic device;
the searching the gesture-to-command map based on the at least one input signal to determine a command comprises searching the gesture-to-command map to determine that the at least one input signal corresponds to the device-specific control command, the device-specific control command corresponding to a second target electronic device in the whitelist; and
the using the at least one wireless communication interface to transmit the target command to the at least one electronic device comprises using the at least one wireless communication interface to transmit the device-specific command to the second target electronic device.

24. The method of claim 15, wherein:
the target command comprises a generic control command;
the sustaining an electronic communication connection to a target electronic device comprises sustaining an electronic communication connection to a first target electronic device;
the searching the gesture-to-command map based on the at least one input signal to determine a target command comprises searching the gesture-to-command map to determine that the at least one input signal corresponds to the generic control command; and
the using the at least one wireless communication interface to transmit the target command to the at least one electronic device comprises using the at least one wireless communication interface to transmit the generic control command to the first target electronic device.

25. The method of claim 15, further comprising using the at least one communication interface to receive data from the at least one electronic device.

26. An assistive device for interacting with at least one electronic device, the assistive device comprising:
a memory to store:
a whitelist including a list of the at least one electronic device; and
a gesture-to-command map comprising a plurality of input signals, each input signal in linked association with one of a plurality of commands, the plurality of commands comprising at least one selection command and at least one control command;
at least one physical interface for receiving at least one input signal from user manipulation of the at least one physical interface;
a gesture analyzer for searching the gesture-to-command map based on the at least one input signal to determine a target command based on the linked command for the at least one input signal; and
at least one communication interface to sustain an electronic communication with a target electronic device that is on the whitelist and to transmit the target command to the target electronic device.

* * * * *